United States Patent
Jung et al.

(10) Patent No.: US 11,692,920 B2
(45) Date of Patent: Jul. 4, 2023

(54) APPARATUS AND METHOD FOR MEASURING IN-SITU CROSSLINK DENSITY AND CROSSLINKED PRODUCT AND METHOD OF FORMING THE SAME

(71) Applicant: Samsung Electronics Co., Ltd., Suwon-si (KR)

(72) Inventors: Young Suk Jung, Suwon-si (KR); Bok Soon Kwon, Suwon-si (KR); Joo Young Kim, Hwaseong-si (KR); Don-Wook Lee, Seoul (KR); Suk Gyu Hahm, Gyungju-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 205 days.

(21) Appl. No.: 17/115,167

(22) Filed: Dec. 8, 2020

(65) Prior Publication Data
US 2021/0223209 A1 Jul. 22, 2021

(30) Foreign Application Priority Data
Jan. 21, 2020 (KR) .................. 10-2020-0008089

(51) Int. Cl.
| | | |
|---|---|---|
| *G01N 9/36* | (2006.01) | |
| *G01N 21/31* | (2006.01) | |
| *G01N 29/04* | (2006.01) | |
| *G01N 29/24* | (2006.01) | |
| *G01N 29/46* | (2006.01) | |

(Continued)

(52) U.S. Cl.
CPC .............. *G01N 9/36* (2013.01); *G01N 9/00* (2013.01); *G01N 9/24* (2013.01); *G01N 21/31* (2013.01);

(Continued)

(58) Field of Classification Search
CPC .. G01N 9/36; G01N 9/24; G01N 9/00; G01N 21/31; G01N 33/442; G01N 2203/0075;

(Continued)

(56) References Cited

U.S. PATENT DOCUMENTS

| | | |
|---|---|---|
| 5,105,655 A | 4/1992 | Khan et al. |
| 7,433,051 B2 | 10/2008 | Owen |

(Continued)

FOREIGN PATENT DOCUMENTS

| | | |
|---|---|---|
| JP | 2006-038533 A | 2/2006 |
| JP | 2009529785 A | 8/2009 |

(Continued)

OTHER PUBLICATIONS

Wang et al., Skin Electronics From Scalable Fabrication of An Intrinsically Stretchable Transistor Array, Mar. 1, 2018, 2018 Macmillan Publishers Limited, Part of Springer Nature, 17 pp. (Year: 2018).*

(Continued)

*Primary Examiner* — Toan M Le
(74) *Attorney, Agent, or Firm* — Harness, Dickey & Pierce, P.L.C.

(57) ABSTRACT

Disclosed are an apparatus for measuring an in-situ crosslink density includes a support configured to fix or support a cross-linkable structure, a light source configured to irradiate light for crosslinking to the cross-linkable structure, and a probe configured to provide in-situ micro-deformation to the cross-linkable structure, wherein the in-situ crosslink density of the cross-linkable structure is measured from a stress-strain phase lag of the cross-linkable structure by the in-situ micro-deformation, a method of measuring the in-situ crosslink density, a method of manufacturing a crosslinked product, a crosslinked product obtained by the method, and a polymer substrate and an electronic device including the crosslinked product.

32 Claims, 16 Drawing Sheets

(51) Int. Cl.
*G01N 9/00* (2006.01)
*G01N 9/24* (2006.01)
*G01N 33/44* (2006.01)

(52) U.S. Cl.
CPC .......... *G01N 29/041* (2013.01); *G01N 29/24* (2013.01); *G01N 29/46* (2013.01); *G01N 33/442* (2013.01); *G01N 2203/0075* (2013.01); *G01N 2203/0092* (2013.01); *G01N 2291/01* (2013.01); *G01N 2291/0235* (2013.01); *G01N 2291/0251* (2013.01)

(58) Field of Classification Search
CPC .......... G01N 2203/0092; G01N 3/405; G01N 2011/004; G01N 11/16; G01N 21/17; G03F 7/7055; C08J 3/24
See application file for complete search history.

(56) References Cited

U.S. PATENT DOCUMENTS

| | | | |
|---|---|---|---|
| 8,069,985 | B2 | 12/2011 | Burattini |
| 9,451,709 | B2 | 9/2016 | Monda et al. |
| 10,414,086 | B2 | 9/2019 | McLeod et al. |
| 2011/0252871 | A1 | 10/2011 | Nagoshi et al. |
| 2012/0118071 | A1 | 5/2012 | Doble et al. |
| 2015/0276684 | A1 | 10/2015 | Seuthe |
| 2016/0077024 | A1 | 3/2016 | Kaneko et al. |
| 2017/0074767 | A1 | 3/2017 | Obie |

FOREIGN PATENT DOCUMENTS

| | | |
|---|---|---|
| JP | 2010504888 A | 2/2010 |
| JP | 2016-166754 A | 9/2016 |
| KR | 10-2001-0009750 A | 2/2001 |
| KR | 10-0308654 B1 | 9/2001 |
| KR | 20150092098 A | 8/2015 |
| KR | 20180004172 A | 1/2018 |
| WO | WO-2012-018140 A1 | 2/2012 |

OTHER PUBLICATIONS

Extended European Search Report dated May 27, 2021 in European Application No. 20217785.3.
Communication pursuant to Article 94(3) EPC dated Sep. 9, 2022 in European Application No. 20217785.3.

* cited by examiner

APPARATUS AND METHOD FOR MEASURING IN-SITU CROSSLINK DENSITY AND CROSSLINKED PRODUCT AND METHOD OF FORMING THE SAME

CROSS-REFERENCE TO RELATED APPLICATION

This application claims priority to and the benefit of Korean Patent Application No. 10-2020-0008089 filed in the Korean Intellectual Property Office on Jan. 21, 2020, the entire contents of which are incorporated herein by reference.

BACKGROUND

1. Field

An apparatus and a method for measuring in-situ crosslink density in a crosslinked product, a crosslinked product, and a method of forming the crosslinked product are disclosed.

2. Description of the Related Art

Manufacturing electronic devices, such as semiconductor devices or display devices, may include applying and processing various materials. It is important, in terms of device reliability, to check whether the material applied or processed at each step has the desired properties.

SUMMARY

Some example embodiments provide an apparatus capable of measuring an in-situ crosslink density of a material.

Some example embodiments provide a method for measuring an in-situ crosslink density of a material.

Some example embodiments provide a method of manufacturing a crosslinked product using the apparatus and/or the method.

Some example embodiments provide a crosslinked product obtained by the method.

Some example embodiments provide a polymer film or an electronic device including the crosslinked product.

According to some example embodiments, an apparatus for measuring an in-situ crosslink density may include a support plate configured to support a cross-linkable structure, a light source configured to irradiate light to the cross-linkable structure, and a probe configured to provide in-situ micro-deformation to the cross-linkable structure, wherein the in-situ crosslink density of the cross-linkable structure is measured from a stress-strain phase lag of the cross-linkable structure during the in-situ micro-deformation.

The light irradiated to the cross-linkable structure may have a wavelength spectrum of less than or equal to about 420 nm.

The apparatus may further include a force sensor and a displacement sensor connected to the probe.

The probe may include a tip positioned at one end of the probe, the tip being configured to contact the cross-linkable structure.

The probe may be configured to repeatedly provide a vibration to the cross-linkable structure during the in-situ micro-deformation.

The apparatus may further include a light-transmitting plate between the light source and the probe.

The light source and the probe may be on an upper portion of the support plate.

The apparatus may further include an electronic controller configured to adjust an intensity of the light source depending on the crosslink density.

According to some example embodiments, an exposure equipment including the apparatus is provided.

According to some example embodiments, a method for measuring an in-situ crosslink density may include preparing a cross-linkable structure, the cross-linkable structure may include a cross-linkable material and a crosslinking agent, irradiating the cross-linkable structure with a light configured to cross-link the cross-linkable structure, providing in-situ micro-deformation to the cross-linkable structure, and measuring the in-situ crosslink density of the cross-linkable structure from a stress-strain phase lag of the cross-linkable structure during the in-situ micro-deformation of the cross-linkable structure.

According to some example embodiments, a method of manufacturing a crosslinked product includes preparing a cross-linkable structure, the cross-linkable structure including a cross-linkable material and a crosslinking agent, and crosslinking the cross-linkable structure by irradiating light onto the cross-linkable structure, wherein the crosslinking of the cross-linkable structure comprises measuring an in-situ crosslink density of the cross-linkable structure by providing in-situ micro-deformation to the cross-linkable structure, and wherein the measuring the in-situ crosslink density of the cross-linkable structure is determined from a stress-strain phase lag of the cross-linkable structure during the in-situ micro-deformation of the cross-linkable structure.

The in-situ micro-deformation of the cross-linkable structure may be performed simultaneously with the irradiating of the light for crosslinking.

The in-situ micro-deformation of the cross-linkable structure may include repeatedly providing vibration to the cross-linkable structure.

The repeatedly providing the vibration to the cross-linkable structure may include vibrating the probe within an elastic section of the cross-linkable structure at a constant displacement in a direction perpendicular to an in-plane direction of the cross-linkable structure.

The repeatedly providing of vibration to the cross-linkable structure may include vibrating a probe so that the strain of the cross-linkable structure may be less than or equal to about 2%.

The repeatedly providing of the vibration to the cross-linkable structure may be performed at a frequency of about 0.05 Hz to about 100 Hz.

A deformation depth of the cross-linkable structure due to the vibration may be less than or equal to about 20% of the length of the cross-linkable structure.

The measuring the in-situ crosslink density of the cross-linkable structure may include calculation of the in-situ crosslink density by Equation 1.

[Equation 1]

$$\text{Crosslink density}(\text{mol}/\text{cm}^3) = \frac{\Delta E' - \left\{ \Delta E'' - (E''_{f_1} - E''_{f_2}) \log \frac{f_2}{f_1} \right\}}{nRT'}$$

In Equation 1,
$\Delta E'$ is an amount of change in a storage modulus,
$\Delta E''$ is an amount of change in a loss modulus,
$f_1$ is a low frequency,
$f_2$ is a high frequency,
$E_{f_1}''$ is an energy loss or a phase lag value at the low frequency, $E_{f2}$" is an energy loss or a phase lag value at the high frequency, n is a proportionality constant, R is a gas constant, and T' is a temperature (K).

The light may have a wavelength spectrum of less than or equal to about 420 nm with an intensity of greater than 0 W/cm² and less than or equal to about 10 W/cm².

The method may further include adjusting an intensity of the light based on the measured crosslink density.

The cross-linkable material may include at least one of a siloxane moiety, a urethane moiety, an olefin moiety, an acrylic moiety, and a photosensitive resin.

The crosslinking of the cross-linkable structure may include disposing a mask on the cross-linkable structure, the mask having a plurality of light-transmitting portions and a light-blocking portion that is a region excluding the light-transmitting portion, and irradiating light through the mask, wherein the lights forms a plurality of crosslinked products, in the cross-linkable structure, at positions corresponding to the plurality of light-transmitting portions.

According to some example embodiments, a crosslinked product obtained by the above method is provided.

According to some example embodiments, a polymer film including the crosslinked product is provided.

According to some example embodiments, an electronic device including the crosslinked product is provided.

An in-situ crosslink density of materials may be measured.

DETAILED DESCRIPTION

Figure 1:
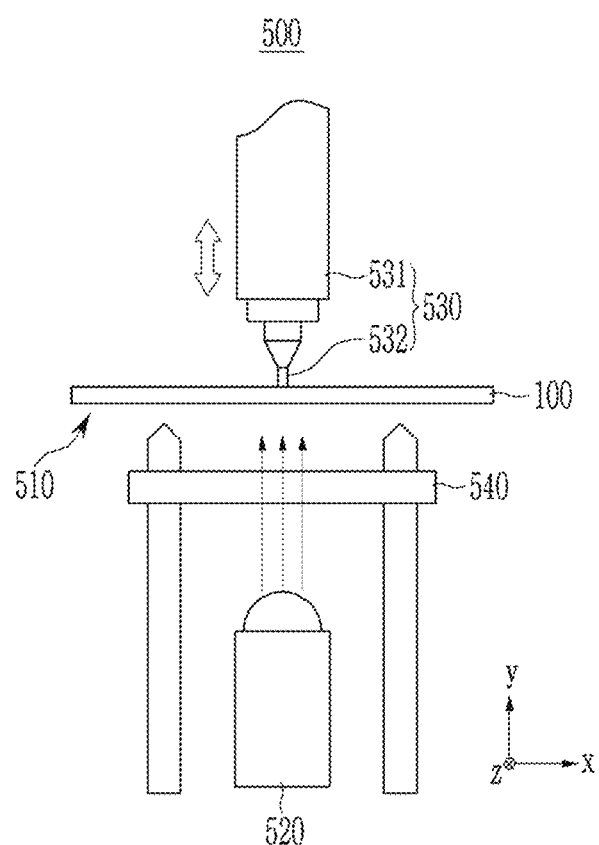
FIG. 1 is a schematic view illustrating an example of an apparatus according to some example embodiments.

Hereinafter, embodiments will be described in detail so that those skilled in the art can easily implement them. However, the actual applied structure may be implemented in various different forms and is not limited to the implementations described herein.

In the drawings, the thickness of layers, films, panels, regions, etc., may be exaggerated for clarity.

Spatially relative terms, such as "lower," "under," "above," "upper," "vertical" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, it will be understood that when an element such as a layer, film, region, or substrate is referred to as being "on" and/or "covering" another element, it may be directly on the other element or intervening elements may also be present. In contrast, when an element is referred to as being "directly on" another element, there are no intervening elements present.

When the terms "about" or "substantially" are used in this specification in connection with a numerical value, it is intended that the associated numerical value includes a manufacturing tolerance (e.g., ±10%) around the stated numerical value. Moreover, when the words "generally" and "substantially" are used in connection with geometric shapes, it is intended that precision of the geometric shape is not required but that latitude for the shape is within the scope of the disclosure. Further, regardless of whether numerical values or shapes are modified as "about" or "substantially," it will be understood that these values and shapes should be construed as including a manufacturing or operational tolerance (e.g., ±10%) around the stated numerical values or shapes.

Hereinafter, the term "combination" includes a mixture and/or two or more stacked structures.

Hereinafter, an example of a device according to an example embodiment is described with reference to the drawings. Some example embodiments provide a measuring apparatus capable of observing an in-situ crosslinking degree for a crosslinking reaction in an apparatus for forming a cross-linkable material into a cross-linked product, and a measuring method using the same.

Figure 2:
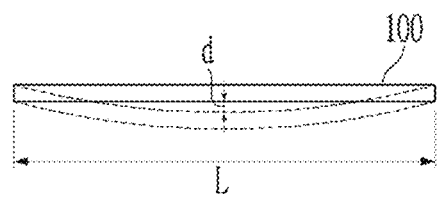
FIG. 2 is a schematic view showing an example of micro-deformation of the cross-linkable structure when using the apparatus of FIG. 1.

FIG. 1 is a schematic view illustrating an example of an apparatus according to some example embodiments, and FIG. 2 is a schematic view showing an example of micro-deformation of the cross-linkable structure when using the apparatus of FIG. 1. Referring to FIG. 1, the apparatus 500 may include a support plate 510, a light source 520, a probe 530, and a light-transmitting plate 540.

The support plate 510 may be configured to fix and/or support an object to be cross-linked (hereinafter, referred to as "cross-linkable structure 100"). The support plate 510 may be a plate configured to support the cross-linkable structure 100. For example, the support plate 510 may fix and/or support a portion of the cross-linkable structure 100 and/or the cross-linkable structure 100 in its entirety. The cross-linkable structure 100 may include, for example, a cross-linkable film including a cross-linkable material and a crosslinking agent, and/or may include, for example, a laminate structure including a cross-linkable layer including a cross-linkable material and a crosslinking agent. The cross-linkable film and/or cross-linkable layer may optionally be on a substrate such as a glass plate or silicon wafer.

The light source 520 may be under the support plate 510 and configured to provide light, for crosslinking the cross-linkable structure 100, to the cross-linkable structure 100. The light source 520 may be configured to irradiate light in a short wavelength spectrum of, for example, less than or equal to about 420 nm. In some example embodiments, the irradiated light may be within a range of less than or equal to about 400 nm and/or less than or equal to about 380 nm. The light source 520 may be configured to irradiate, for example, ultraviolet light (UV), extreme ultraviolet light (EUV) and/or X-rays, but is not limited further. The light source 520 may be configured to irradiate light in a wavelength spectrum of less than or equal to about 420 nm with an intensity greater than about 0 W/cm$^2$ and less than or equal to about 10 W/cm$^2$.

The light-transmitting plate 540 may be between the cross-linkable structure 100 and the light source 520 such that light emitted from the light source 520 may be projected onto the cross-linkable structure 100. For example, the light-transmitting plate 540 may be over the light source 520 and/or under the support plate 510. The light-transmitting plate 540 may have a transmittance of greater than or equal to about 80% for a spectrum of light for crosslinking the cross-linkable structure 100. For example, the light-transmitting plate 540 may have a transmittance greater than or equal to about 85%, greater than or equal to about 90%, greater than or equal to about 95%, and/or greater than or equal to about 98% for the spectrum of light for crosslinking the cross-linkable structure 100. The light-transmitting plate 540 may be configured to filter light outside of the spectrum of light for crosslinking the cross-linkable structure 100. In some example embodiments, the light-transmitting plate 540 may include, for example, quartz, but is not limited thereto. A mask and/or filter (not illustrated) including a pattern to be transferred to the cross-linkable structure 100 may be included on the light-transmitting plate 540.

The probe 530 may include a dynamic probe configured to move in at least a direction. For example, the probe 530 may be configured to move in a vertical direction (e.g., a y-direction) perpendicular to a plane (e.g., a plane including the x-z directions) of the cross-linkable structure 100. The probe 530 may include a rod 531 and a tip 532 at one end of the rod 531. The rod 531 may have a cylindrical shape, but is not limited thereto. The tip 532 may be a portion of the probe 530 configured to contact the cross-linkable structure 100 during the movement of the probe 530. The tip 532 may have a diameter within the micrometer scale (e.g., between 1 μm to 9 mm in scale). For example, the tip 532 may have a diameter of tens of micrometers to hundreds of micrometers. The probe 530 may be over the center of the support plate 510, on the opposite side of the light source 520. The probe 530 may be, for example, configured to be on the support plate 510.

The probe 530 may be configured to provide an in-situ micro-deformation to the cross-linkable structure 100. The in-situ micro-deformation may including causing periodic contact between the probe 530 and the surface of the cross-linkable structure 100. The periodic contact may result in non-destructive deformation such as compression and/or tension on the surface of the cross-linkable structure 100. For example, a strain of the cross-linkable structure 100, introduced by the non-destructive deformation, may be less than or equal to about 2%, and may be in the range of greater than about 0% and less than or equal to about 1.5%, greater than about 0% and less than or equal to about 1% and/or greater than about 0% and less than or equal to about 0.5%, but is not limited thereto.

The probe 530 may be configured to repeatedly provide vibration to the cross-linkable structure 100 for in-situ micro-deformation. The vibration may be, for example, an oscillatory vibration. The oscillatory vibration may be vibration that proceeds at a constant amplitude within a frequency. For example, within an elastic section of the cross-linkable structure 100, the probe 530 may be configured to vibrate repeatedly with a constant displacement in the vertical direction (e.g., y-direction).

For example, the micro-deformation (e.g., oscillatory vibration) of the probe 530 may be performed such that a strain of the cross-linkable structure 100 may be less than or equal to about 2%, and within the range of greater than about 0% and less than or equal to about 1.5%, greater than about 0% and less than or equal to about 1%, or greater than about 0% and less than or equal to about 0.5%, but is not limited thereto.

For example, the micro-deformation (e.g., oscillatory vibration) of the probe 530 may be performed at a frequency of about 0.01 Hz to about 100 Hz, about 0.05 Hz to about 100 Hz, about 0.05 Hz to about 80 Hz, about 0.05 Hz to about 50 Hz, and/or about 0.05 Hz to about 30 Hz, but is not limited thereto.

The probe 530 may be connected to a force sensor and/or a displacement sensor. The force sensor may measure a dynamic force such as compression and/or tension, and it may be configured to sense stress and/or strain applied to the cross-linkable structure 100 within the elastic section of the cross-linkable structure 100 and/or fed-back from the cross-linkable structure 100. The displacement sensor may measure a distance between the probe 530 and the cross-linkable structure 100, for example a distance of the probe 530 above and/or in the cross-linkable structure 100. The displacement sensor may be, therefore, configured to detect whether the probe 530 is vibrating, within an elastic section of the cross-linkable structure 100, within a displacement value. The displacement value may include, for example, a predetermined range.

The probe 530 may periodically contact the surface of the cross-linkable structure 100 through such vibration to cause in-situ (real-time) micro-deformation. Such an in-situ micro-deformation may be performed simultaneously with light irradiation using the light source 520. For example, the in-situ micro-deformation may start with the "on" of the light source 520 and end with the "off" of the light source 520.

Referring to FIG. 2, the deformation depth (d) of the cross-linkable structure 100 due to vibration of the probe 530 may be, for example, less than or equal to about 20%, less than or equal to about 15%, less than or equal to about 10%, and/or less than or equal to about 5% of the length (L) of the cross-linkable structure 100.

The cross-linkable structure 100 receiving the vibration of the probe 530 may exhibit a phase lag between the applied stress and/or strain and the fed-back strain and/or stress. The stress-strain phase lag may depend on an elastic modulus change related to a change in the molecular structure of the cross-linkable structure 100, for example by the initiation and/or propagation of cross-linking chemistry within the cross-linkable structure 100, and thus may be used as an index for examining a crosslinking degree of the cross-linkable structure 100. Accordingly, the stress-strain phase lag SSPL of the cross-linkable structure 100 may be used to measure in-situ crosslink density of the cross-linkable structure 100.

Figure 3:
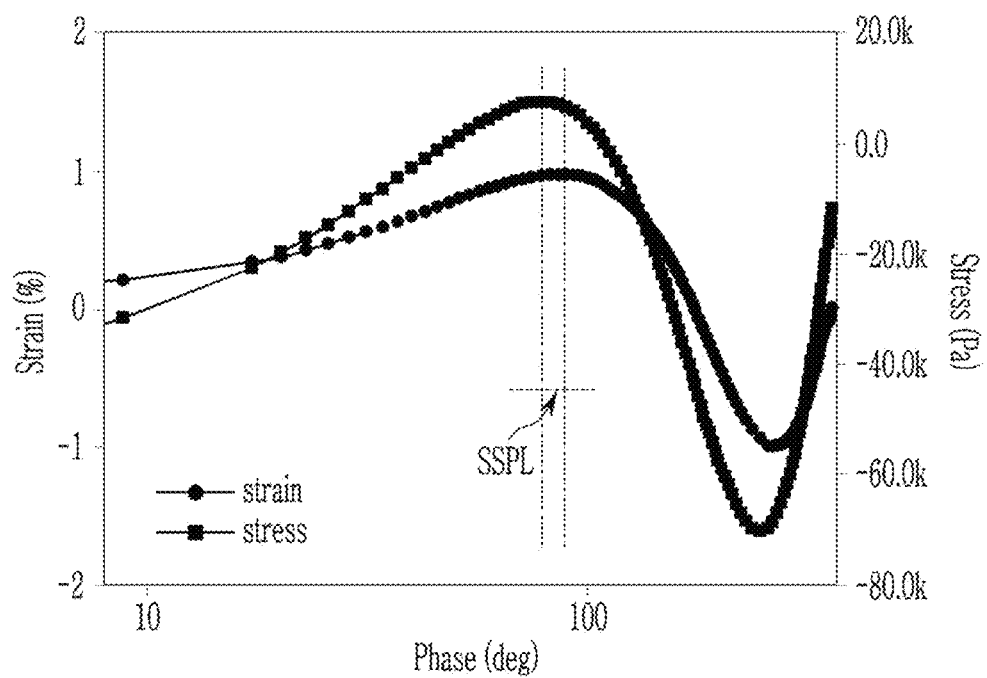
FIG. 3 is a graph of a stress-strain phase lag according to one example.

FIG. 3 is a graph of a stress-strain phase lag according to one example.

Referring to FIG. 3, the stress-strain phase lag SSPL between the applied stress and/or strain and the fed-back strain and/or stress appears and may be used to confirm the crosslinking degree of the cross-linkable structure 100. The stress-strain phase lag SSPL may be changed depending on a strain rate (e.g., frequency), for example, when a phase of the semi-crystalline cross-linkable structure 100 is changed from an elastic state to a visco-elastic state, and/or from a flow state to the visco-elastic state. For example, as the strain rate increases, the stress-strain phase lag may increase.

The crosslink density of the cross-linkable structure 100 may be calculated from a change in a feedback time depending on a frequency, and may be calculated based on a change in the storage modulus and/or the loss modulus of the cross-linkable structure 100.

The storage modulus may be determined by a chemical bond included in the cross-linkable material and/or the entanglement and/or interpenetration of polymer chains, wherein in-situ crosslink density may be obtained by reflecting an in-situ storage modulus and an energy loss according to a light irradiation, while compensating for the polymer chain entanglement effect due to a frequency difference and a pure storage modulus increment according to a crosslinking reaction.

For example, the crosslink density of the cross-linkable structure 100 may be calculated by Equation 1.

[Equation 1]

$$\text{Crosslink density(mol/cm}^3) = \frac{\Delta E' - \left\{ \Delta E'' - (E''_{f_1} - E''_{f_2}) \log \frac{f_2}{f_1} \right\}}{nRT'}$$

In Equation 1,
ΔE' is an amount of change in the storage modulus,
ΔE" is an amount of change in the loss modulus,
$f_1$ is a low frequency,
$f_2$ is a high frequency,
$E_{f_1}''$ is an energy loss or a phase lag value at the low frequency,
$E_{f_2}''$ is an energy loss or a phase lag value at the high frequency,
n is a proportionality constant,
R is a gas constant, and
T' is a temperature (K) at the time of measurement.

Equation 1 is derived from Flory Equation and may include subtracting the loss modulus, except for an energy loss depending on the strain rate (e.g., frequency), from the storage modulus of the cross-linkable structure 100.

For example, a crosslinking degree may be a ratio of the crosslink density relative to the number of moles of a cross-linkable functional group per unit volume of the cross-linkable material, for example, according to Equation 2.

$$\text{Crosslinking degree(\%)} = \frac{\text{Crosslink density}}{D} \times 100 \quad \text{[Equation 2]}$$

In Equation 2, D is the number of moles of the cross-linkable functional group per unit volume (mol/cm³) of the cross-linkable material.

The apparatus 500 may further include an electronic controller (not shown) connected to the light source 520 and/or the probe 530. The controller may be configured to control the light irradiation, for example, by stopping the light irradiation for crosslinking when calculated crosslink density reaches desired crosslink density. The controller may also be configured to receive signals from the probe 530, to control the in-situ micro-deformation of the cross-linkable structure 100 by controlling the depth and/or frequency of the oscillation of the probe 530. For example, the controller may control the depth of oscillation by the probe 530 based on signals received from the displacement sensor. The controller may also control the oscillation of the probe 530 and/or "on/off" state of the light source 520 based on signals received from the force sensor. The controller may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), and programmable logic unit, a microprocessor, application-specific integrated circuit (ASIC), etc.

This apparatus 500 may be used to obtain information with respect to the crosslink density of the cross-linkable structure 100 through a non-destructive analysis, and accordingly, an in-situ crosslinking degree according to a crosslinking reaction may be examined to stop crosslinking at the desired crosslinking density and, thus, obtain crosslinked products having desired properties. Accordingly, unlike a conventional crosslinking degree-measurement method, regardless of whether the number of crosslinking reaction sites of the cross-linkable material is greater or less than the number of reaction sites of the crosslinking agent, the apparatus 500 may be effectively applied.

The apparatus 500 may be included in exposure equipment used in the production of a crosslinking film and/or an electronic device (e.g., a semiconductor device and/or a display device). The exposure equipment may be used to obtain information with respect to in-situ crosslink density of a cross-linkable layer included in the crosslinking film and/or the electronic device through the non-destructive analysis, and accordingly, the in-situ crosslinking degree in the crosslinking reaction is observed to stop crosslinking at a desired crosslinking density and thus obtain crosslinked products having desired properties. In addition, when a plurality of cross-linkable layers included in the crosslinking film and/or the electronic device are crosslinked in a continuous process, the crosslinked products having a substantially constant crosslink density may be continuously produced, and accordingly, since the crosslinked products having constant crosslink density may be obtained without deviation, the reproducibility and reliability of the crosslinked products may be increased.

Hereinafter, another example of the apparatus according to some example embodiments will be described with reference to drawing.

Figure 4:
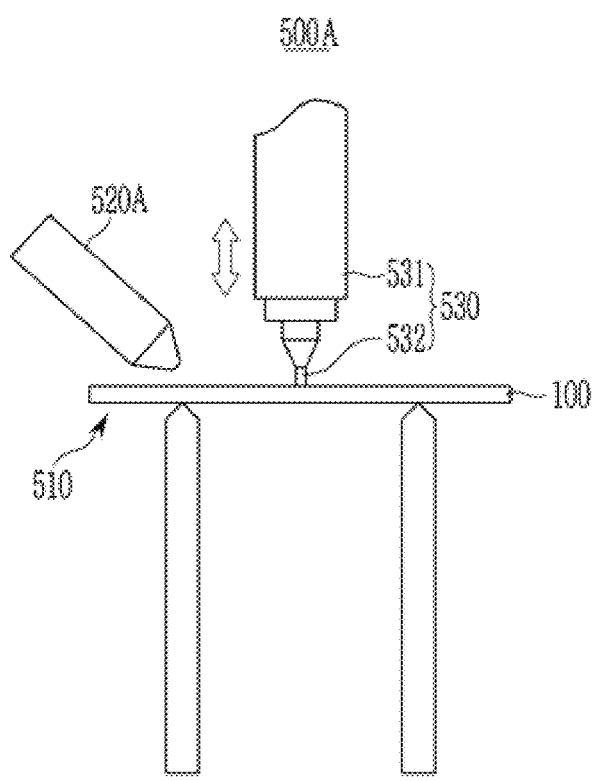
FIG. 4 is a schematic view illustrating another example of an apparatus according to some example embodiments.

FIG. 4 is a schematic view illustrating another example of an apparatus according to some example embodiments.

Referring to FIG. 4, the apparatus 500A according to some example embodiments includes a support plate 510; a light source 520A; and a probe 530 including a rod 531 and a tip 532. In describing FIG. 4, descriptions that overlap with those of FIG. 1 will be omitted.

In the apparatus 500A, according to some example embodiments, the light source 520A is over the upper portion of the support plate 510 like the probe 530, unlike the aforementioned example embodiments illustrated in FIG. 1. Furthermore, the light-transmitting plate 540 may be omitted. The light source 520A may be configured to irradiate light to the top and/or side of the cross-linkable structure 100. Accordingly, even when the cross-linkable structure 100 is on an opaque substrate, such as a silicon wafer, it may be crosslinked by light as described above.

Hereinafter, an example of a method for measuring the in-situ crosslink density using the aforementioned apparatuses 500 and 500A is described.

A method of measuring an in-situ crosslink density may include, for example preparing a cross-linkable structure 100, irradiating light for crosslinking to the cross-linkable structure 100, providing in-situ micro-deformation to the cross-linkable structure 100, and measuring the in-situ crosslink density of the cross-linkable structure 100 from a stress-strain phase lag of the cross-linkable structure 100 by the in-situ micro-deformation of the cross-linkable structure 100.

Such an in-situ crosslink density measurement may be applied in the manufacture of crosslinked products from the cross-linkable structure 100, and when the crosslinked products are manufactured, the method of measuring an in-situ crosslink density may be applied to verify the in-situ crosslink density.

That is, an example of a method of manufacturing the crosslinked product may include preparing a cross-linkable structure 100 and crosslinking a cross-linkable structure 100 by irradiating light, wherein the crosslinking of the cross-linkable structure 100 may include measuring the in-situ crosslink density of the cross-linkable structure 100 according to the method described above. For example, the measuring the in-situ crosslink density of the cross-linkable structure 100 may include providing an in-situ micro-deformation to the cross-linkable structure 100, and measuring the in-situ crosslink density of the cross-linkable structure 100 from the stress-strain phase lag of the cross-linkable structure 100 by the in-situ micro-deformation of the cross-linkable structure 100.

The cross-linkable structure 100 may include a mixture of a cross-linkable material and a crosslinking agent.

The cross-linkable material may include a cross-linkable monomer, a cross-linkable oligomer, a cross-linkable polymer including a cross-linkable functional group, and/or a combination thereof. The cross-linkable material may be a material exhibiting, for example, visco-elastic behavior, and may be a cross-linkable elastomer. The cross-linkable material may, for example, include a siloxane moiety such as polydimethylsiloxane (PDMS); an olefin moiety such as styrene-ethylene-butylene-styrene (SEBS); a urethane moiety; an acryl moiety; a photosensitive resin, and/or a combination thereof, but is not limited thereto.

The crosslinking agent may be a crosslinking agent configured to initiate a crosslinking reaction. For example, the crosslinking agent may be an optical crosslinking agent initiated by light irradiation. The crosslinking agent may include at least one cross-linkable functional group, for example an azido group, a cyano group, an isocyanate group, an epoxy group, or a combination thereof, but is not limited thereto. The crosslinking agent may be included in an amount of about 0.01 to 50 parts by weight. For example, the crosslinking agent may be included within the range of about 0.1 to 30 parts by weight based on 100 parts by weight of the cross-linkable material.

The preparing of the cross-linkable structure 100 may include mixing a cross-linkable material and a crosslinking agent in a solvent; coating the mixture on a substrate, and drying the substrate. In another example embodiment, the preparing of the cross-linkable structure 100 may include mixing the cross-linkable material and a crosslinking agent and melt-blending the mixture at a temperature equal to or higher than the glass transition temperature (Tg) of the cross-linkable material.

The irradiating the light for crosslinking to the cross-linkable structure may include irradiating light to the lower, upper and/or side surfaces of the cross-linkable structure 100. The irradiated light may include a wavelength spectrum of less than or equal to about 420 nm, for example, ultraviolet (UV) light, extreme ultraviolet (EUV) light, and/or an X-ray, and may include an intensity of greater than 0 W/cm$^2$ and less than or equal to about 10 W/cm$^2$. The irradiating may include an exposure time of about 1 minute to about 10 hours, but the types of light, the light intensity, and/or the exposure time may be variously changed.

The providing the cross-linkable structure 100 with an in-situ micro-deformation may include contacting the cross-linkable structure 100 with the probe 530, as described above. The contracting the cross-linkable structure 100 with the probe 530 may be a real-time operation. For example, as described above, the probe 530 may be repeatedly vibrated under a constant displacement in a direction vertical to the in-plane directions of the cross-linkable structure 100 in an elastic section of the cross-linkable structure 100.

The micro-deformation (e.g., oscillatory vibration) may be performed such that a strain of the cross-linkable structure 100 is less than or equal to about 2%, and may be within the range of greater than about 0% and less than or equal to about 1.5%, greater than 0% and less than or equal to about 1%, and/or greater than 0% and less than or equal to about 0.5%, but is not limited thereto.

The deformation depth (d) of the cross-linkable structure 100 due to vibration by micro-deformation (e.g., oscillatory vibration) may be less than or equal to about 20%, less than or equal to about 15%, less than or equal to about 10%, and/or less than or equal to about 5% of the length (L) of the cross-linkable structure 100.

The micro-deformation (e.g., oscillatory vibration) may be performed at a frequency of about 0.01 Hz to about 100 Hz, for example, within the range of about 0.05 Hz to about 100 Hz, about 0.05 Hz to about 80 Hz, about 0.05 Hz to about 50 Hz, and/or about 0.05 Hz to about 30 Hz, but is not limited thereto.

The micro-deformation (e.g., oscillatory vibration) may be simultaneously performed with the light irradiation, for example, simultaneously "on" with a start of the light irradiation and "off" with an end of the light irradiation The crosslink density of the cross-linkable structure 100 may be observed in situ (real time) from a phase lag between the stress and/or strain applied to the cross-linkable structure 100 and the strain and/or stress fed back therefrom, and calculated based on a change of the storage modulus and the loss modulus. For example, the change in crosslink density of the cross-linkable structure 100 may be calculated through Equation 1. This crosslink density may be used to calculate a crosslinking degree, for example, through Equation 2.

A desired crosslink density for the cross-linkable structure 100 may be set and/or predetermined, and when the measured crosslink density reaches the desired crosslink density, the crosslinking reaction conditions may be terminated. For example, when the measured crosslink density reaches the desired crosslink density, the light irradiation for crosslinking may be controlled (e.g., dimmed and/or stopped). Accordingly, the cross-linkable structure 100 may be crosslinked in the above method to obtain crosslinked products having a desired crosslink density.

Such a method may be used to obtain in-situ (real time) information with respect to crosslink density of the cross-linkable structure 100 through the non-destructive analysis, and thereby an in-situ crosslinking degree in the crosslinking reaction is observed to stop the crosslinking at desired crosslink density and obtain crosslinked products having desired properties. Accordingly, unlike the conventional crosslinking degree-measuring method, this method may be effectively applied, regardless of whether the number of crosslinking reaction sites of a cross-linkable material is greater than or less than the number of reaction sites of a crosslinking agent.

The crosslinked product may be, for example, a polymer film and/or a photosensitive film, but is not limited thereto.

Hereinafter, a polymer film according to some example embodiments is described.

The polymer film according to some example embodiment may be a stretchable film including an elastomer and may be used as a stretchable substrate of an electronic device.

Figure 5:
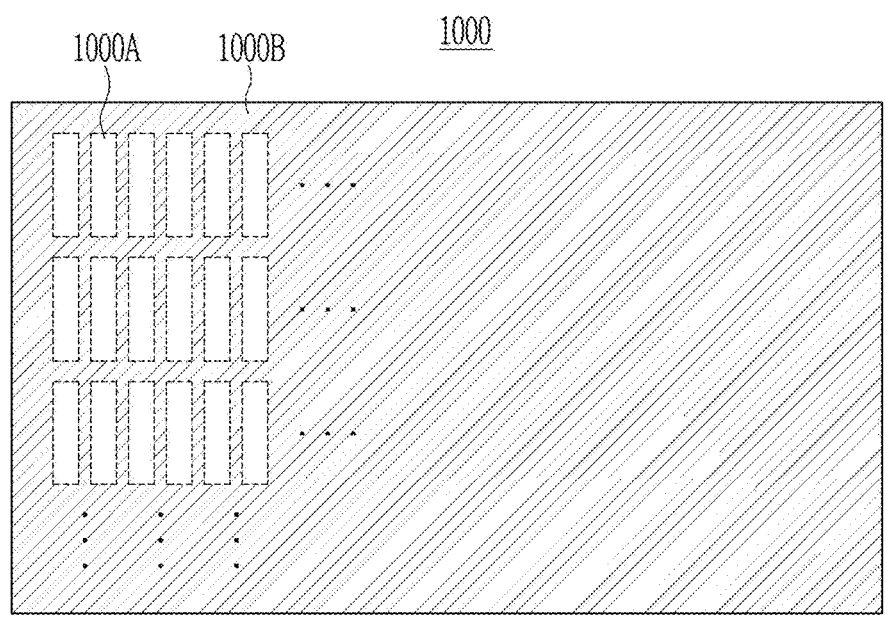
FIG. 5 is a top plan view schematically showing a polymer film according to some example embodiments.

FIG. 5 is a top plan view schematically showing a polymer film according to some example embodiments.

The polymer film 1000 according to some example embodiment may include an elastomer. The elastomer may include, for example, a polyorganosiloxane such as polydimethylsiloxane (PDMS), a butadiene moiety such as styrene-ethylene-butylene-styrene (SEBS), a urethane moiety, an acrylic moiety, an olefin moiety, and/or a combination thereof, but is not limited thereto.

Referring to FIG. 5, the polymer film 1000 may include regions with different elastic moduli. For example, the polymer film 1000 may include a plurality of first regions 1000A having a relatively high elastic modulus and a second region 1000B having a lower elastic modulus than that of the first region 1000A. An elastic modulus difference of the first region 1000A and the second region 1000B of the polymer film 1000 may be greater than or equal to about 100 times. For example, the elastic modulus of the first region 1000A may be greater than or equal to about 100 times that of the second region 1000B. The elastic modulus of the first region 1000A may be about 100 to 100,000 times larger than that of the second region 100B, but is not limited thereto. For example, the elastic modulus of the first region 1000A may be about $10^7$ Pa to about $10^{12}$ Pa, and the elastic modulus of the second region 1000B may be greater than or equal to about $10^2$ Pa and/or less than about $10^7$ Pa, but is not limited thereto.

The elongation rates of the first region 1000A and the second region 1000B of the polymer film 1000 may be different due to the difference in the elastic modulus described above. For example, the elongation rate of the second region 1000B may be greater than the elongation rate of the first region 1000A. Here, the elongation rate may be a percentage of a length change that is increased to a breaking point relative to an initial length. For example, the elongation rate of the first region 1000A of the polymer film 1000 may be less than or equal to about 5%, and within the range of about 0% to about 5%, about 0% to about 4%, about 0% to about 3%, about 0% to about 2%, about 0% to about 1%, about 0.5% to about 5%, about 0.5% to about 4%, about 0.5% to about 3%, about 0.5% to about 2%, and/or about 1% to about 2%. For example, the elongation rate of the second region 1000B of the polymer film 1000 may be greater than or equal to about 10%, and within the range of about 10% to about 300%, about 10% to about 200%, about 10% to about 100%, about 10% to about 90%, about 10% to about 80%, about 10% to about 70%, about 10% to about 60%, about 10% to about 50%, about 10% to about 40%, about 20% to about 70%, about 20% to about 60%, about 20% to about 50%, and/or about 20% to about 40%.

The plurality of first regions 1000A of the polymer film 1000 may be island-shaped and separated from each other. The plurality of first regions 1000A may include a matrix arrangement repeatedly arranged along rows and/or columns. The plurality of first regions 1000A of the polymer film 1000 may include the crosslinked products obtained from the aforementioned cross-linkable structure 100, and may include the unit elements described later.

The second region 1000B of the polymer film 1000 may include the remainder of the polymer film 1000, excepting for a plurality of the first regions 1000A, and be continuously connected. The second region 1000B of the polymer film 1000 may provide the polymer film 1000 with stretchability, a net relatively low elastic modulus, and a net high elongation rate. Thus the polymer film 1000 may flexibly respond to an external force and/or an external motion such as twisting, pressing, and pulling, and thus be easily recovered therefrom.

The polymer film 1000 may be obtained by crosslinking the cross-linkable structure 100, as described above. For example, a mask having a plurality of light-transmitting portions and a light-blocking portion may be prepared and disposed between the cross-linkable structure 100 and the light source 520 and/or 520A. Then, the cross-linkable structure 100 may be irradiated by light from the light source 520 and/or 520A to crosslink the portions of the cross-linkable structure 100 corresponding to the plurality of light-transmitting portions and thus form the plurality of the first regions 1000A including crosslinked products.

Figure 6:
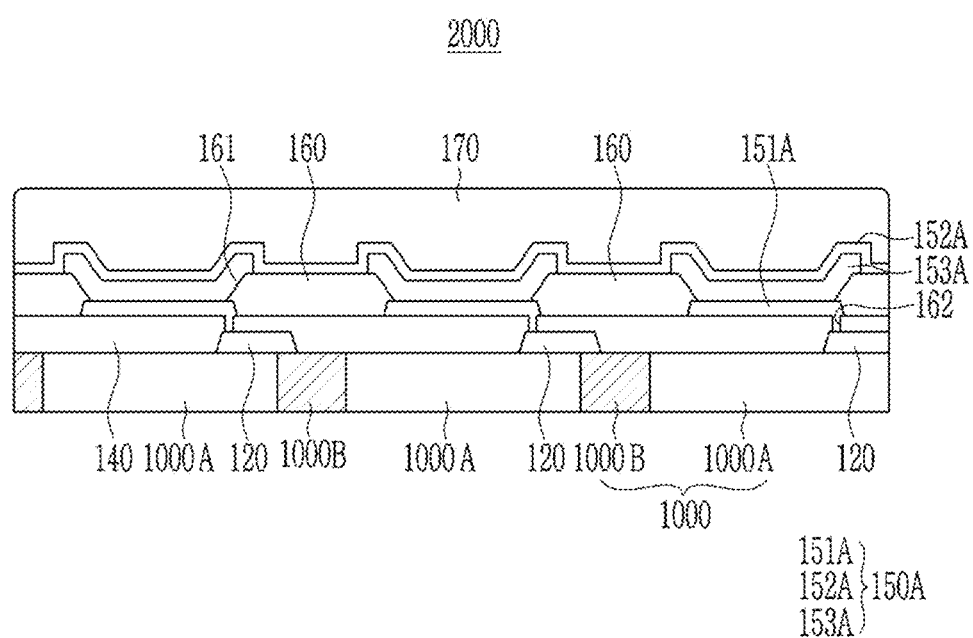
FIG. 6 is a cross-sectional view showing an example of an electronic device including the polymer film of FIG. 5 as a substrate.

FIG. 6 is a cross-sectional view showing an example of an electronic device including the polymer film of FIG. 5 as a substrate.

Referring to FIG. 6, the electronic device 2000 includes a polymer film 1000 including the first regions 1000A and the second region 1000B; a transistor 120 on the polymer film 1000; an insulating layer 140; a pixel-defining layer 160, unit element 150A; and an encapsulant 170.

Each of the transistors 120 may be on the first regions 1000A of the polymer film 1000, the second region 1000B of the polymer film 1000, and/or across the first and second regions 1000A and 1000B of the polymer film 1000. In some example embodiments, when the transistor 120 is on second region 1000B of the polymer film 1000, the transistor 120 may be a stretchable transistor.

One or more transistors 120 may be included in each pixel and each transistor 120 may be connected to a plurality of signal lines (not shown). The plurality of signal lines may include a gate line configured to transfer a gate signal (and/or a scan signal), a data line configured to transfer a data signal, and a driving voltage line configured to transfer a driving voltage. At least a part of the plurality of signal lines may include a stretchable wire.

The transistor 120 may include, for example, a switching transistor and/or a driving transistor. The switching transistor may be electrically connected to the gate line and the data line and may include a first gate electrode connected to the gate line; a first source electrode connected to the data line; a first drain electrode facing the first source electrode; and a first semiconductor electrically connected to the first source electrode and the first drain electrode, respectively. The driving transistor may include a second gate electrode electrically connected to the first drain electrode; a second source electrode connected to the driving voltage line; a second drain electrode facing the second source electrode; and a second semiconductor electrically connected to the second source electrode and the second drain electrode, respectively. The first semiconductor and the second semiconductor may each include a semiconductor material and an elastomer. For example, the first semiconductor and the second semiconductor may each include an organic semiconductor material and an elastomer.

The insulating layer 140 may include an organic and/or inorganic insulating material, for example, an inorganic insulating material such as silicon oxide, silicon nitride, and silicon oxynitride; an organic insulating materials such as polyimide; and/or an organic/inorganic insulating material such as polyorganosiloxane or polyorganosilazane. The insulating layer 140 may include a stretchable insulating layer and may include, for example, an elastomer. The elastomer may include the aforementioned organic elastomer, organic/inorganic elastomer, inorganic elastomer-like material, or a combination thereof, but is not limited thereto. The insulating layer 140 may include a plurality of contact holes 162 exposing the transistor 120.

A unit element array is formed on the insulating layer 140. The unit element array may include a plurality of unit elements 150A repeatedly aligned along a column and/or a row, and the plurality of unit elements 150A may be respectively on the first regions 1000A of the polymer film 1000. For example, the alignment of the plurality of unit elements 150A may be the same as the alignment of the first regions 1000A of the polymer film 1000. Each unit element 150A may include, for example, a diode and/or a transistor.

The plurality of unit elements 150A may include a plurality of pixel electrodes 151A respectively isolated on the plurality of first regions 1000A of the polymer film 1000; a common electrode 152A; and a plurality of active layers 153A between the pixel electrode 151A and the common electrode 152A. In an example embodiment, the common electrode 152A may be cover a whole surface of the polymer film 1000.

The unit element 150A including the pixel electrode 151A, the common electrode 152A, and the active layer 153A may be on the first region 1000A of the polymer film 1000 including crosslinked products having relatively high crosslink density. Accordingly, the unit element 150A may not receive substantial influences from an external force or an external motion such as twisting, pressing, and pulling of the electronic device 2000, and accordingly, a material for improving performance of the pixel electrode 151A, the common electrode 152A, and the active layer 153A may be freely selected, and in addition, a damage or destruction due to tensile deformation according to the external force or the external motion may be reduced or prevented.

Each of the pixel electrode 151A and the common electrode 152A may be independently include a low-resistance conductor such as a metal, a conductive oxide, a conductive carbon, and/or a conductive organic material. For example, the pixel electrode 151A and the common electrode 152A may each independently include a metal such as aluminum, silver, gold, copper, magnesium, nickel, molybdenum, and/or an alloy thereof; conductive oxide such as indium tin oxide (ITO), indium zinc oxide (IZO), zinc tin oxide (ZTO), aluminum tin oxide (ATO), and/or aluminum zinc oxide (AZO); a conductive carbon such as graphene and/or carbon nanotubes (CNT); and/or a conductive organic material such as polyacetylene (PA), polypyrrole (PPy), polythiophene (PT), polyaniline (PA), and/or poly(3,4-ethylenedioxythiophene).

The pixel electrode 151A and/or the common electrode 152A may include a transparent and/or opaque electrode. The transparent electrode may have a transmittance of greater than or equal to about 80% and may include, for example, a thin film metal, the conductive oxide, the conductive organic material, and/or the carbon conductor described above, and the opaque electrode may have a transmittance of less than about 10% and/or a reflectivity of greater than or equal to about 5%, and may include, for example, a metal.

Each pixel electrode 151A may be electrically connected to the transistor 120 in each pixel, and each pixel may be driven independently. A common voltage may be applied to the common electrode 152A.

The active layer 153A may include a light emitting layer and/or a photoelectric conversion layer.

The light emitting layer may include an organic material, an inorganic material, an organic/inorganic material, and/or a combination thereof configured to emit light. For example, the light emitting layer may include an organic light emitting material, a quantum dot, a perovskite material, and/or a combination thereof, but is not limited thereto.

When the light emitting layer includes an organic light emitting material, the unit element 150A may be an organic light emitting diode. When the light emitting layer includes a quantum dot, the unit element 150A may be a quantum dot light emitting diode. When the light emitting layer includes a perovskite material, the unit element 150A may be a perovskite light emitting diode.

The photoelectric conversion layer may be configured to absorb light in at least a portion of the wavelength spectrum and convert the absorbed light into an electrical signal. For example, the photoelectric conversion layer may be configured to convert light in at least one of a blue wavelength spectrum (hereinafter referred to as "blue light"), a green wavelength spectrum (hereinafter referred to as "green light"), a red wavelength spectrum (hereinafter referred to as "red light"), and/or an infrared wavelength spectrum (hereinafter referred to as "infrared light") into an electrical signal.

For example, the photoelectric conversion layer may be configured to selectively absorb at least one of the blue light, the green light, the red light, and/or the infra-red light and to convert the absorbed light into an electrical signal. Herein, the selective absorption of at least one of the blue light, the green light, the red light, and the infra-red light means that an absorption spectrum has a maximum absorption wavelength (Amax) in one of greater than or equal to about 380 nm and less than about 500 nm (e.g., blue light), about 500 nm to about 600 nm (e.g., green light), greater than about 600 nm and less than or equal to about 700 nm (e.g., red light), and/or greater than about 700 nm and less than or equal to about 3000 nm (e.g., infra-red light), and wherein an absorption spectrum in the corresponding wavelength spectrum is significantly higher than those in the other wavelength spectrums. Herein "significantly higher" may mean that about 70% to about 100%, about 75% to about 100%, about 80% to about 100%, about 85% to about 100%, about 90% to about 100%, and/or about 95% to about 100% relative to a total area of the absorption spectrum may belong to the corresponding wavelength spectrum.

The photoelectric conversion layer may include, for example, a p-type semiconductor and an n-type semiconductor and may be configured to forming a p-n junction. At least one of the p-type semiconductor and the n-type semiconductor may be a light absorbing material, and at least one of the p-type semiconductor and the n-type semiconductor may be a light absorbing material having wavelength selectivity. For example, at least one of the p-type semiconductor and the n-type semiconductor may have a maximum absorption wavelength (Amax) in a wavelength spectrum of greater than or equal to about 380 nm and less than about 500 nm, about 500 nm to about 600 nm, greater than about 600 nm and less than or equal to about 700 nm, and greater than about 700 nm and less than or equal to about 3000 nm. The p-type semiconductor and the n-type semiconductor may have a peak absorption wavelength ($\lambda_{max}$) in the same and/or different wavelength spectrums. The p-type semiconductor and the n-type semiconductor may include an organic material, an inorganic material, and/or an organic/inorganic material. For example, at least one of the p-type semiconductor and the n-type semiconductor may be an organic material.

The unit element 150A may further include an auxiliary layer (not shown) between the pixel electrode 151A and the active layer 153A and/or between the common electrode 152A and the active layer 153A. The auxiliary layer may be, for example, a charge auxiliary layer, a light emitting auxiliary layer, and/or a light absorbing auxiliary layer. The charge auxiliary layer may include, for example, one or more layers selected from a hole injection layer, a hole transport layer, an electron blocking layer, an electron injection layer, an electron transport layer, and/or a hole blocking layer. The auxiliary layer may include an organic material, an inorganic material, and/or an organic/inorganic material.

The pixel definition layer 160 may be on a whole surface of the insulating layer 140 and may be, for example, a continuous film including a plurality of openings 161. The plurality of openings 161 may be on the first region 1000A of the polymer film 1000 and may define each pixel and expose each unit element 150A. For example, the shape and size of each pixel may be determined according to the shape and size of each opening 161.

The encapsulant 170 may cover a whole surface of the polymer film 1000 and may be configured to effectively block and/or prevent the inflow of oxygen, moisture, and/or contaminants from the outside. For example, when the electronic device 2000 is a display device or a sensor attached to or included in a living body, the encapsulant 170 may prevent biological secretions such as sweat from flowing into the electronic device 2000 and thus prevent and/or slow the degradation of the electronic device 2000.

As described above, the electronic device 2000 includes the polymer film 1000 including the aforementioned cross-linked product as a substrate. The polymer film 1000 may include a first region 1000A having a relatively high cross-link density and a low elongation rate and a second region 10008 having a low crosslink density and a high elongation rate. Therefore, it is possible to flexibly respond to external forces or external movements such as twisting, pressing, and pulling in any direction without damaging the unit element 150A.

In addition, the electronic device 2000 includes the unit element 150A on the first region 1000A of the polymer film 1000. Thereby tensile deformation of the unit element 150A may be prevented and thus inhibit or prevent damage and/or destruction when the polymer film 1000 is stressed and/or strained by an external force and/or an external motion, and a material for improving the performance of the components constituting the unit element 150A may be freely selected.

The aforementioned electronic device 2000 may be applied to various devices requiring stretchability, for example, a wearable device, a skin-like device, and a large-area conformable display, smart clothing, and the like, but is not limited thereto.

For example, the aforementioned electronic device 2000 may be included in a skin display panel and/or an attachable biological sensor.

The skin display panel may be an ultrathin display panel and may be attached to a portion of a living body such as a hand. The skin display panel may be configured to display visual information such as various characters and/or images. The skin display panel may include, for example, an inorganic light emitting diode, a micro light emitting diode, an organic light emitting diode, a quantum dot light emitting diode, and/or a perovskite light emitting diode, but is not limited thereto.

The attachable biological sensor may be configured to attach to a surface of a living body (e.g., skin), implanted into inside the living body (e.g., on and/or in an internal organ), and/or through indirect to contact with the living body (e.g., clothing), and to detect and measure biological information such as a biological signal. As an example, the attachable biosensor may include an electroencephalogram (EGG) sensor, an electrocardiogram (ECG) sensor, a blood pressure (BP) sensor, an electromyography (EMG) sensor, a blood glucose (BG) sensor, a photoplethysmography (PPG) sensor, an accelerometer, an RFID antenna, an inertial sensor, an activity sensor, a motion sensor, and/or a combination thereof, but is not limited thereto. The attached biological sensor may be attached to a living body in a very thin patch-type or band-shaped form, so that biological information may be monitored in real time.

Figure 7:
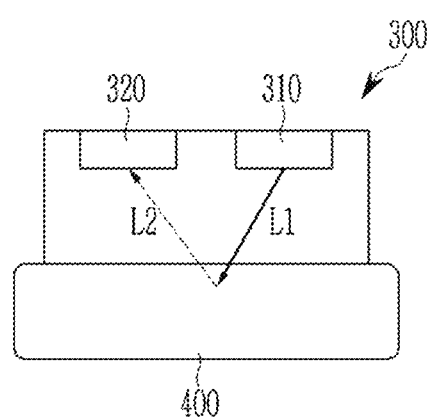
FIG. 7 is a schematic view showing an example of an operation of a biological sensor according to some example embodiments.

FIG. 7 is a schematic view showing an example of an operation of a biological sensor according to some example embodiments.

Referring to FIG. 7, the biological sensor 300 includes a light emitting device 310 and a photoelectric conversion device 320. The light emitting device 310 may include, for example, an inorganic light emitting diode, an organic light emitting diode, and/or a micro light emitting diode. The photoelectric conversion device 320 may include, for example, a photodiode and/or a photoelectric conversion layer.

The light emitting device 310 may be configured to emit a first light L1 for sensing a biosignal. The light emitting device 310 may be, for example, an infrared light emitting diode configured to emit the first light L1 in an infrared wavelength spectrum and/or a visible light emitting diode configured to emit the first light L1 in a visible wavelength spectrum. The first light L1 emitted from the light emitting device 310 may be configured to be reflected and/or absorbed by an object 400 (e.g., a structure included in a living body, such as a skin or blood vessel). The light emitting device 310 may include the electronic device 2000.

The photoelectric conversion device 320 may be configured to receive a second light L2 reflected by the object 400, and may be configured to convert it into an electrical signal. The electrical signal converted from the reflected second light L2 may include bio-information. The electrical signals may be transmitted to a sensor IC (not shown) and/or a processor (not shown). As an example, the biological sensor 300 may be a photoplethysmogram (PPG) sensor. The bio-information may include, for example, heart rate, oxygen saturation, stress, arrhythmia, blood pressure, etc. and may be obtained by analyzing a waveform of an electrical signal. The photoelectric conversion device 320 may include the electronic device 2000.

The aforementioned skin display panel and/or attachable biological sensor may be included in various electronic devices, and the electronic device may further include a processor (not shown) and a memory (not shown).

Hereinafter, the embodiments are illustrated in more detail with reference to some example embodiments. However, these embodiments are merely examples, and the present scope is not limited thereto.

Preparation of Cross-linkable Structure

Preparation Example 1

A styrene-ethylene-butylene-styrene (SEBS) base polymer (Asahi Kasei Company) is added to 1.0 ml of toluene at a concentration of 30 wt %; 0.6 parts by weight of a crosslinking agent represented by Chemical Formula A based on 100 parts by weight of the base polymer is added thereto and then, stirred therewith to prepare a cross-linkable solution. Subsequently, the cross-linkable solution is spin-coated on a glass substrate at 400 rpm and then, dried to form a 50 μm-thick cross-linkable layer.

Figure 8:
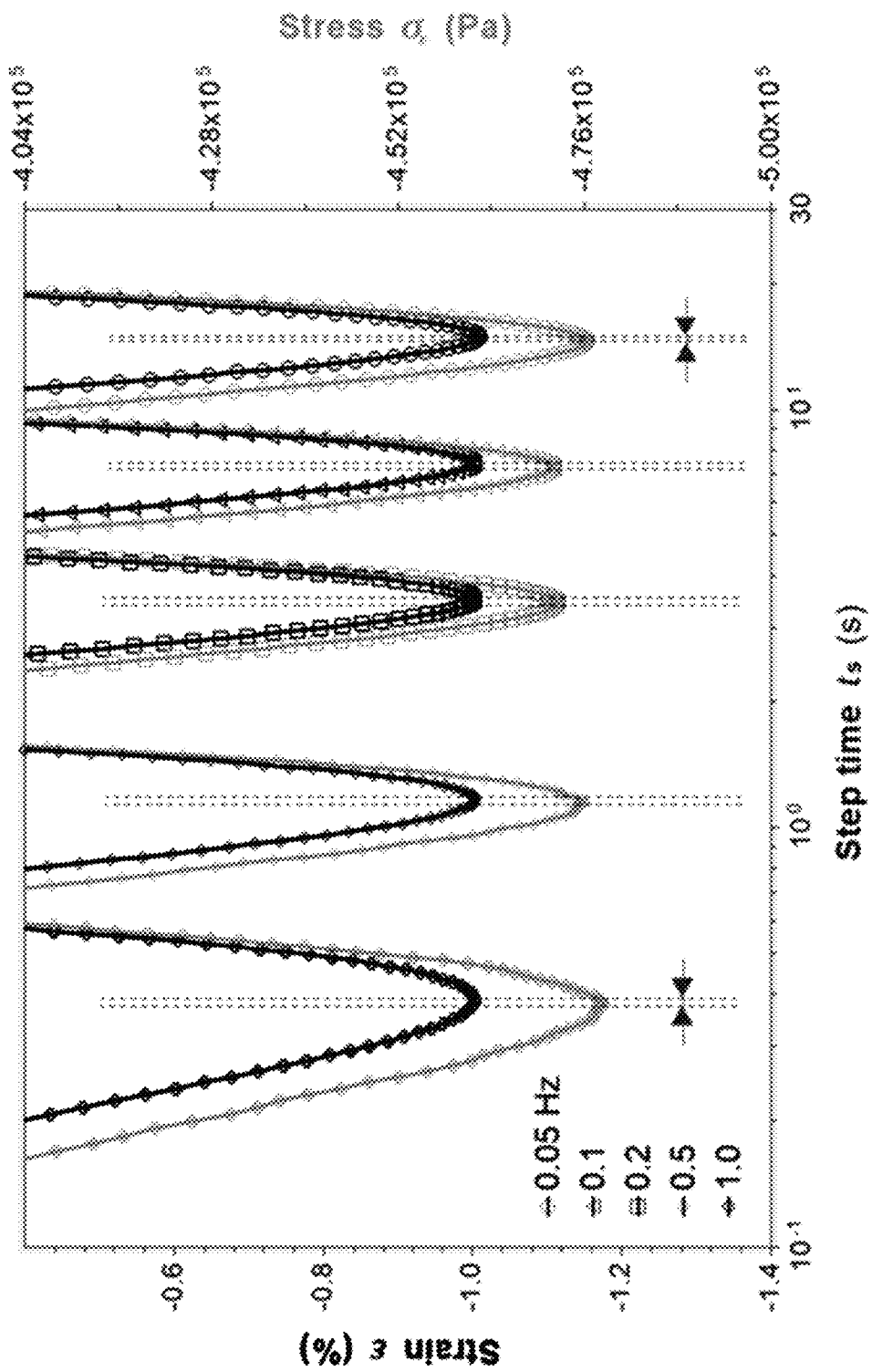
FIG. 8 is a graph showing a stress-strain phase lag according to the crosslinking time observed in Example 1 (frequencies of 0.05 Hz, 0.1 Hz, 0.2 Hz, 0.5 Hz, and 1.0 Hz)
Figure 9:
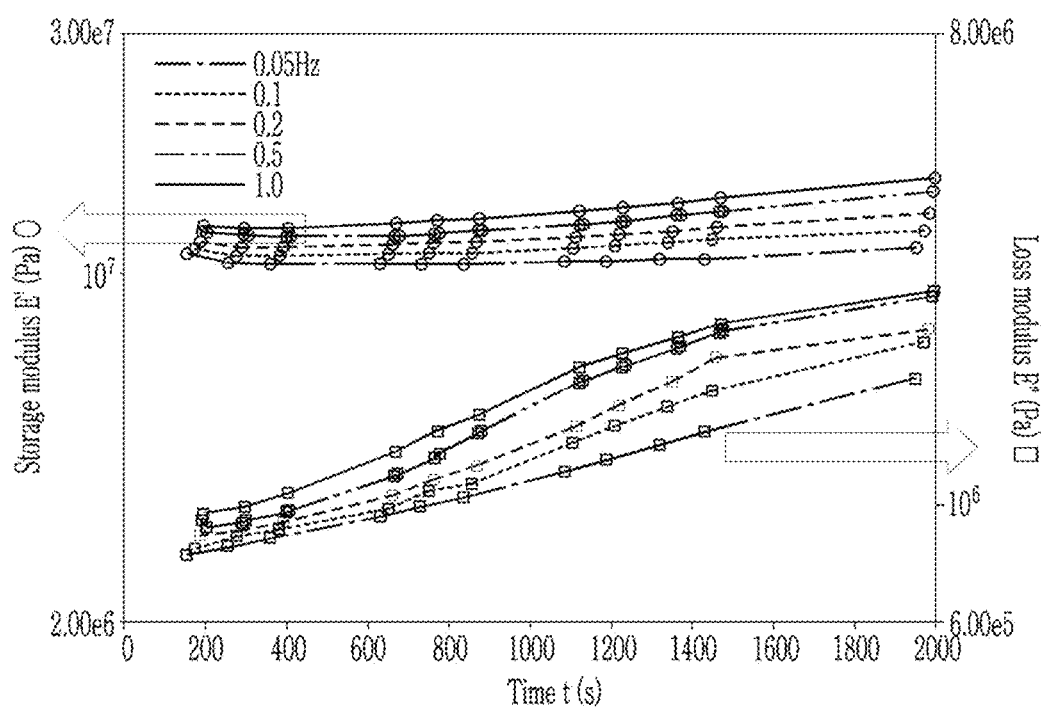
FIG. 9 is a graph showing a change in elastic energy storage modulus and loss modulus over time observed in Example 1 (frequencies of 0.05 Hz, 0.1 Hz, 0.2 Hz, 0.5 Hz, and 1.0 Hz)
Figure 10:
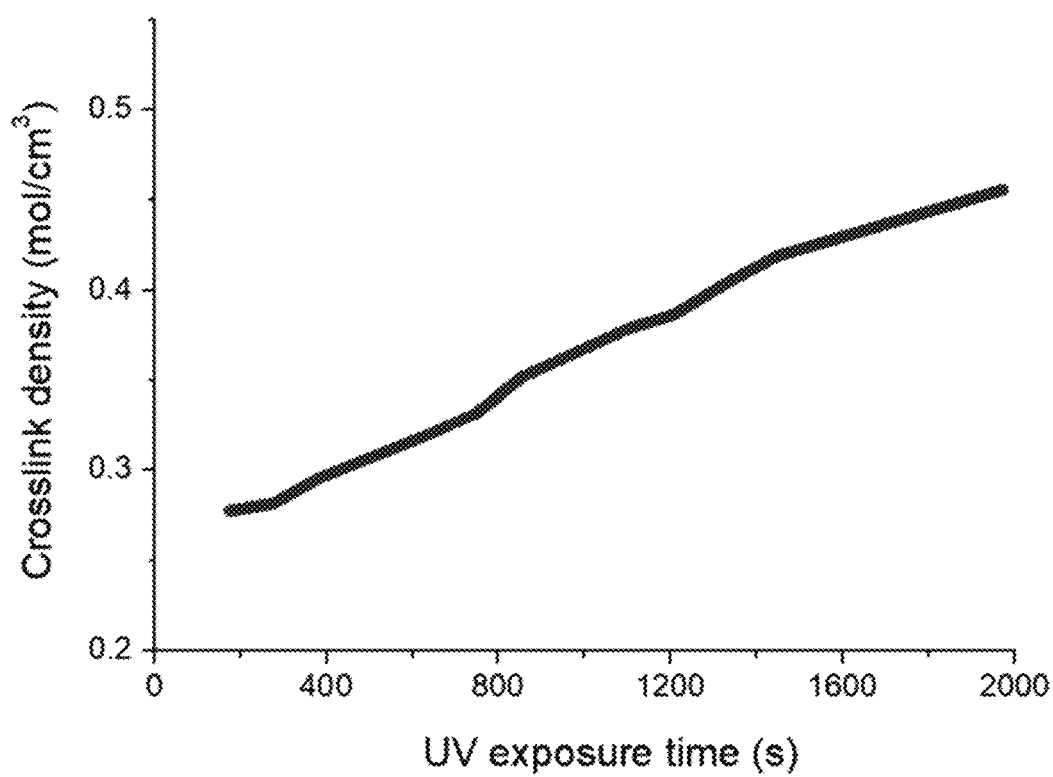
FIG. 10 is a graph showing a change in crosslink density according to crosslinking time in Example 1.

FIG. 8 is a graph showing a stress-strain phase lag according to the crosslinking time observed in Example 1 (frequencies of 0.05 Hz, 0.1 Hz, 0.2 Hz, 0.5 Hz, and 1.0 Hz), FIG. 9 is a graph showing a change in elastic energy storage modulus and loss modulus over time observed in Example 1, and FIG. 10 is a graph showing a change in crosslink density according to crosslinking time in Example 1.

Referring to FIG. 8, phase lags appear between stress applied to the cross-linkable layer and fed-back strain for each frequency (0.05 Hz, 0.1 Hz, 0.2 Hz, 0.5 Hz, and 1.0 Hz).

Table 1 shows the stress-strain phase lag value according to each frequency in FIG. 8.

TABLE 1

| Frequency (Hz) | Stress-strain phase lag (degrees) |
| --- | --- |
| 0.05 Hz | 5.40 |
| 0.1 Hz | 5.52 |
| 0.2 Hz | 5.59 |
| 0.5 Hz | 5.70 |
| 1.0 Hz | 5.76 |

When examined in consideration of this stress-strain phase lag effect of FIG. 8 and Table 1 depending on UV irradiation time, as shown in FIG. 9, the storage modulus and the loss modulus of the cross-linkable layer are increased during an exposure time, an in-situ crosslink density change graph depending from the exposure time may be obtained as shown in FIG. 10 through Equation 1 ($f_1$=0.05 Hz, $f_2$=1.0 Hz).

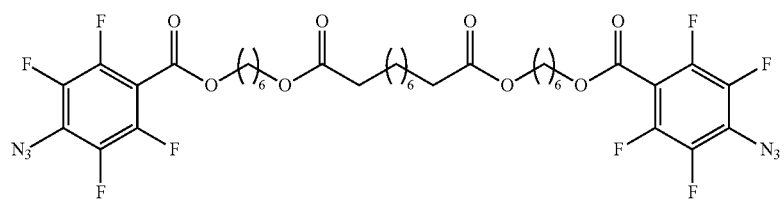

[Chemical Formula A]

Preparation Example 2

A cross-linkable layer is formed according to the same method as Preparation Example 1 except that 20 parts by weight of the crosslinking agent based on 100 parts by weight of the base polymer is used.

Measurement of Crosslink Density I

Example 1

The cross-linkable layer of Preparation Example 1 is irradiated by UV light (a wavelength: 264 nm) with exposure intensity of 1.3 mW/cm² for 30 minutes, and simultaneously, a probe is used to repeatedly provide a vibration corresponding to a frequency of 0.001 to 100 Hz (ex. 0.05 Hz, 0.1 Hz, 0.2 Hz, 0.5 Hz, 1.0 Hz) on the surface of the cross-linkable layer, a stress-strain phase lag and changes of a storage modulus and a loss modulus are evaluated, which are used to evaluate a change of crosslink density according to Equation 1.

Measurement of Crosslink Density II

Example 2

A crosslink density change is evaluated according to the same method as Example 1 except that the cross-linkable layer of Preparation Example 1 is irradiated by UV light with exposure intensity of 1.8 mW/cm² instead of the exposure intensity of 1.3 mW/cm².

Figure 11:
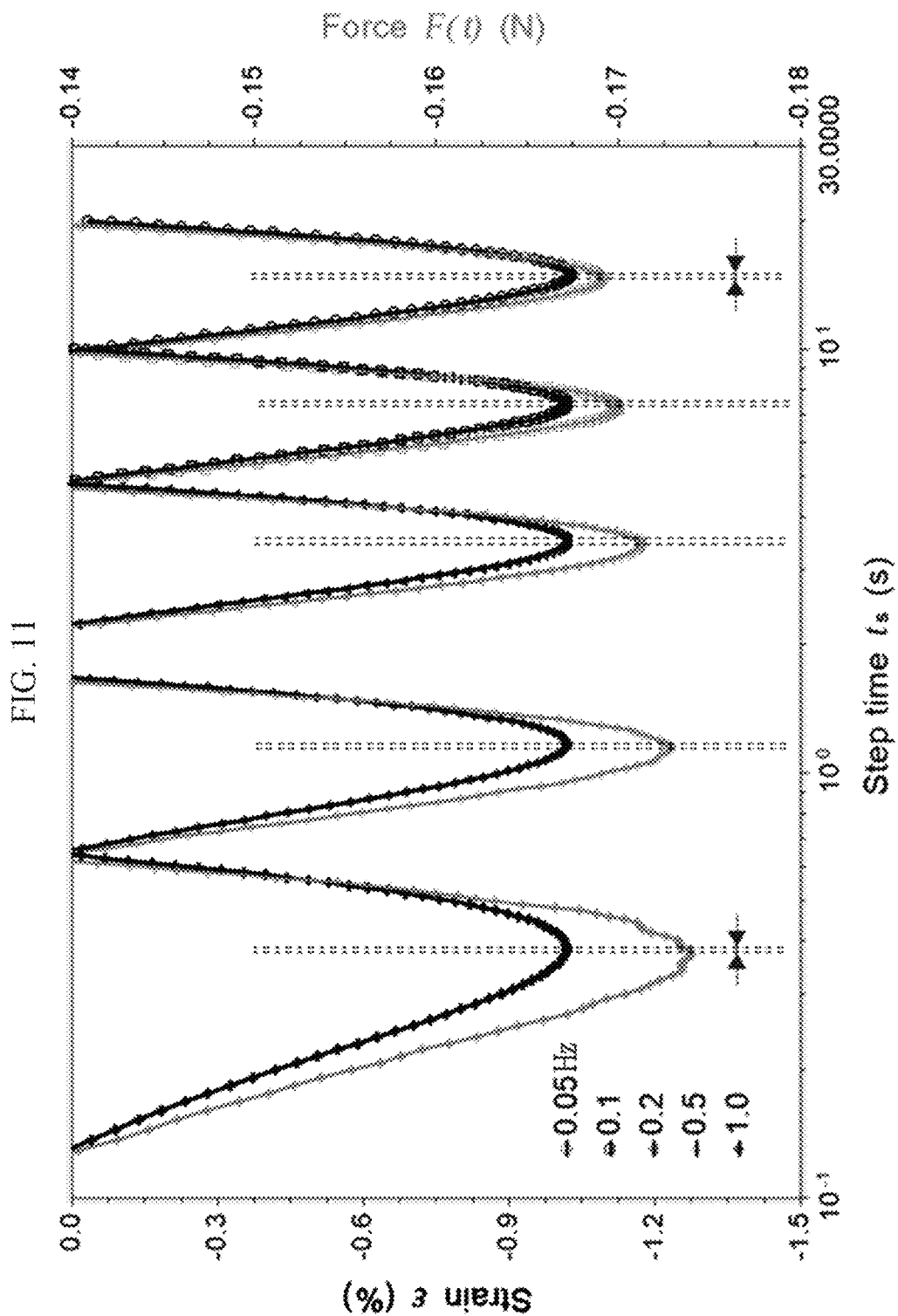
FIG. 11 is a graph showing a stress-strain phase lag observed in Example 2 (frequencies of 0.05 Hz, 0.1 Hz, 0.2 Hz, 0.5 Hz, and 1.0 Hz)
Figure 12:
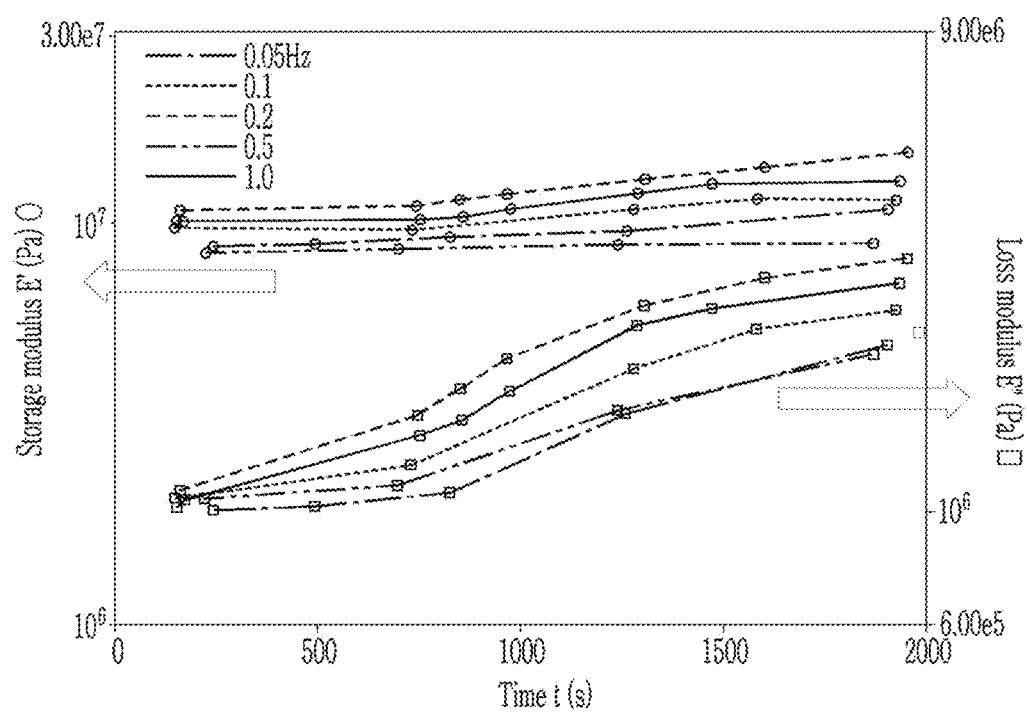
FIG. 12 is a graph showing a change in elastic energy storage modulus and loss modulus over time observed in Example 2 (frequencies of 0.05 Hz, 0.1 Hz, 0.2 Hz, 0.5 Hz, and 1.0 Hz)
Figure 13:
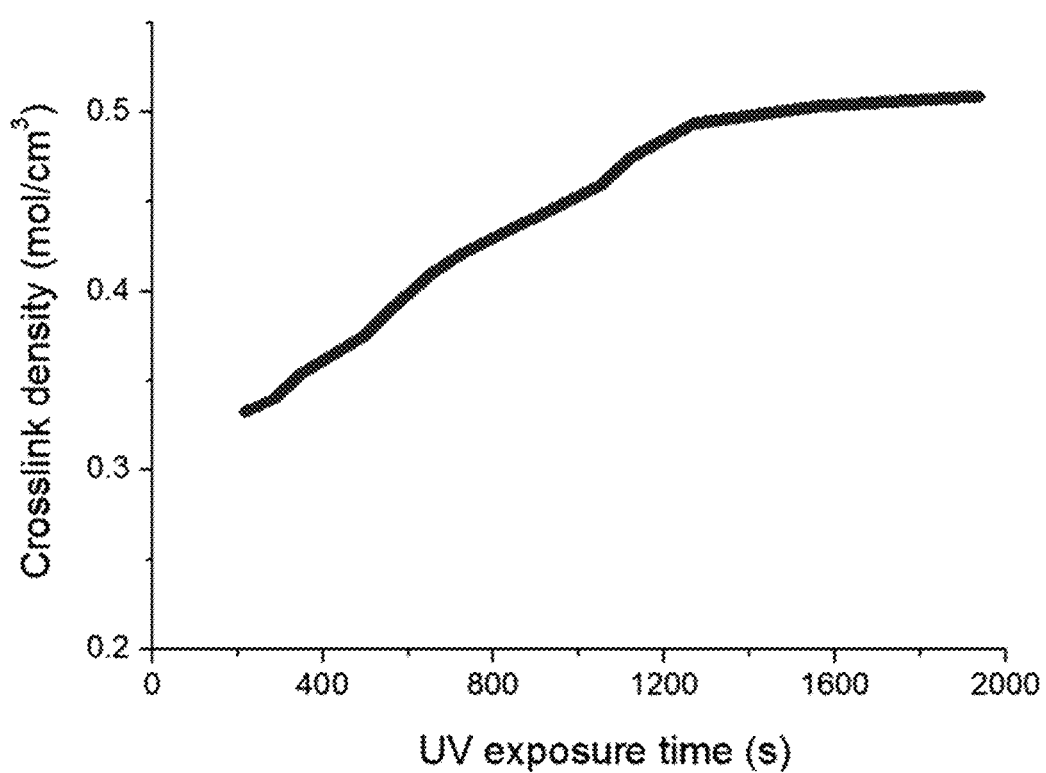
FIG. 13 is a graph showing the crosslink density of the crosslinked layer obtained according to Example 2.

FIG. 11 is a graph showing a stress-strain phase lag observed in Example 2 (frequencies of 0.05 Hz, 0.1 Hz, 0.2 Hz, 0.5 Hz, and 1.0 Hz), FIG. 12 is a graph showing a change in elastic energy storage modulus and loss modulus over time observed in Example 2, and FIG. 13 is a graph showing the crosslink density of the crosslinked layer obtained according to Example 2.

Referring to FIG. 11, phase lags appear between stress applied to the cross-linkable layer and fed-back strain for each frequency (0.05 Hz, 0.1 Hz, 0.2 Hz, 0.5 Hz, and 1.0 Hz).

Table 2 shows the stress-strain phase lag value according to each frequency in FIG. 11.

TABLE 2

| Frequency (Hz) | Stress-strain phase lag (degrees) |
|---|---|
| 0.05 Hz | 5.42 |
| 0.1 Hz | 5.46 |
| 0.2 Hz | 5.50 |
| 0.5 Hz | 5.52 |
| 1.0 Hz | 5.60 |

When examined in consideration of the stress-strain phase lag effect of FIG. 11 and Table 2 depending on UV irradiation time, as shown in FIG. 12, the storage modulus and the loss modulus of the cross-linkable layer increase over time, and an in-situ crosslink density change graph depending on exposure time is obtained through Equation 1 ($f_1$=0.05 Hz, $f_2$=1.0 Hz) as shown in FIG. 13. Referring to FIG. 13, when the exposure intensity is increased, crosslink density may exhibit saturation after a predetermined exposure time.

Measurement of Crosslink Density III

Example 3

A crosslink density change is evaluated according to the same method as Example 1 except that the cross-linkable layer of Preparation Example 2 is used instead of the cross-linkable layer of Preparation Example 1.

Figure 14:
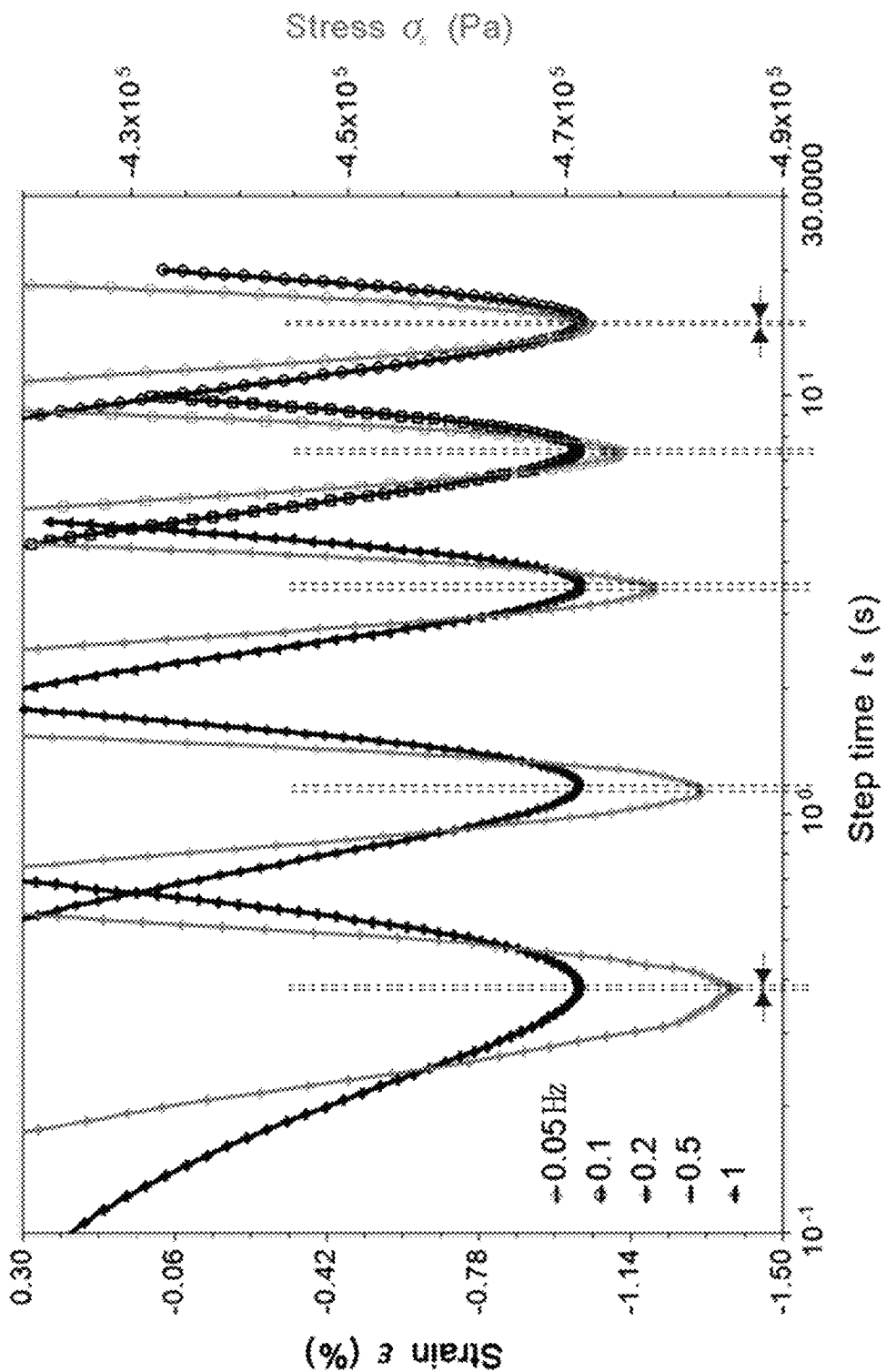
FIG. 14 is a graph showing a stress-strain phase lag observed in Example 3 (frequencies of 0.05 Hz, 0.1 Hz, 0.2 Hz, 0.5 Hz, and 1.0 Hz)
Figure 15:
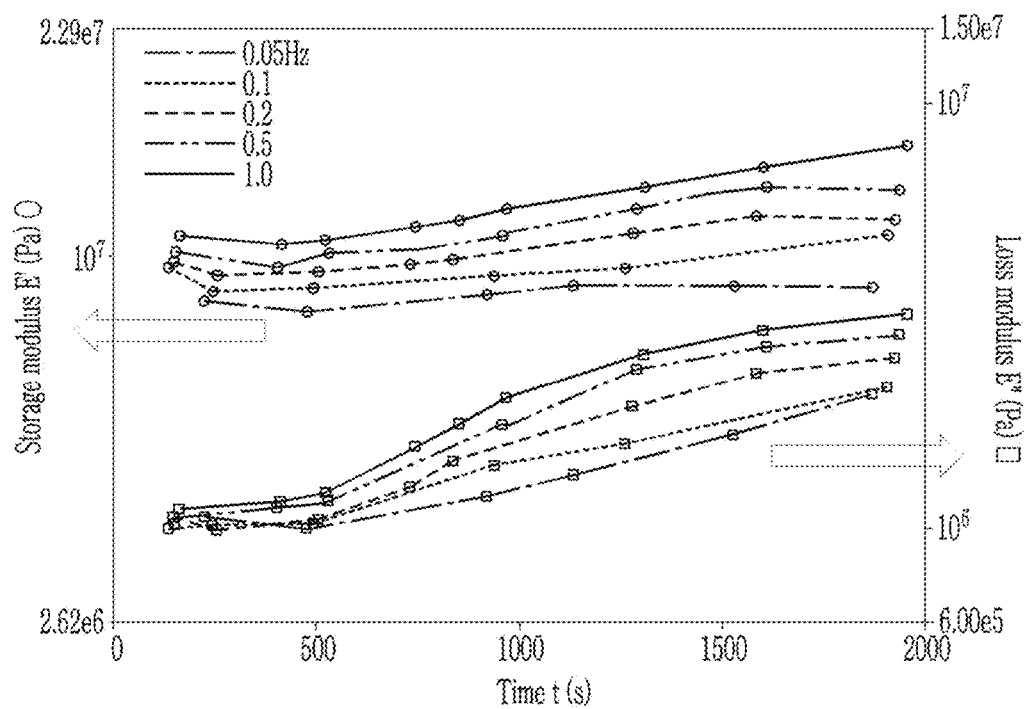
FIG. 15 is a graph showing a change in elastic energy storage modulus and loss modulus over time observed in Example 3 (frequencies of 0.05 Hz, 0.1 Hz, 0.2 Hz, 0.5 Hz, and 1.0 Hz)
Figure 16:
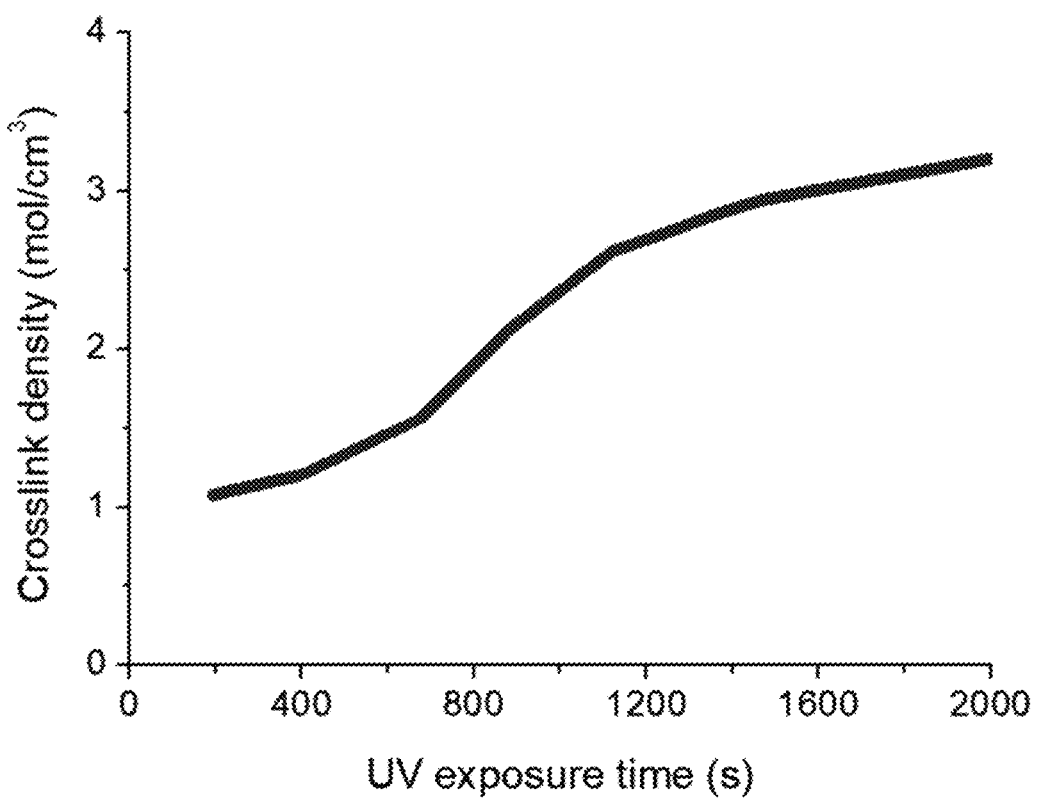
FIG. 16 is a graph showing the crosslink density of the crosslinked layer obtained according to Example 3.

FIG. 14 is a graph showing a stress-strain phase lag observed in Example 3 (frequencies of 0.05 Hz, 0.1 Hz, 0.2 Hz, 0.5 Hz, and 1.0 Hz), FIG. 15 is a graph showing a change in elastic energy storage modulus and loss modulus over time observed in Example 3, and FIG. 16 is a graph showing the crosslink density of the crosslinked layer obtained according to Example 3.

Referring to FIG. 14, phase lags appear between stress applied to the cross-linkable layer and fed-back strain for each frequency (0.05 Hz, 0.1 Hz, 0.2 Hz, 0.5 Hz, and 1.0 Hz).

Table 3 shows the stress-strain phase lag value according to each frequency in FIG. 14.

TABLE 3

| Frequency (Hz) | Stress-strain phase lag (degrees) |
|---|---|
| 0.05 Hz | 5.42 |
| 0.1 Hz | 5.44 |
| 0.2 Hz | 5.51 |
| 0.5 Hz | 5.53 |
| 1.0 Hz | 5.56 |

In consideration of the stress-strain phase lag effect of FIG. 14 and Table 3, when examined according to UV exposure time, the storage modulus and the loss modulus of the cross-linkable layer are increased, as shown in FIG. 15, and an in-situ crosslink density change graph may be obtained according to Equation 1 ($f_1$=0.05 Hz, $f_2$=1.0 Hz), as shown in FIG. 16. Referring to FIG. 16, in the cross-linkable layer according to Preparation Example 2 using an excess amount of the crosslinking agent, as an amount of the crosslinking agent is greater than a number of reaction sites in a cross-linkable material, saturated crosslink density may be exhibited when exposed to a predetermined exposure dose.

While this disclosure has been described in connection with what is presently considered to be practical example embodiments, it is to be understood that the invention is not limited to the disclosed embodiments. On the contrary, it will be understood by those of ordinary skill in the art that various changes in form and details may be made therein without departing from the spirit and scope as defined by the following claims.

What is claimed is:

1. An apparatus for measuring an in-situ crosslink density, comprising:
   a support plate configured to support a cross-linkable structure;
   a light source configured to cross-link the cross-linkable structure by irradiating light to the cross-linkable structure;
   a probe configured to induce a stress-strain phase lag of the cross-linkable structure by providing in situ micro-deformation to the cross-linkable structure during the irradiating of the cross-linkable structure; and
   an electronic controller configured to control the light source based on the in-situ crosslink density of the cross-linkable structure,
   wherein the in-situ crosslink density of the cross-linkable structure is measured from the stress-strain phase lag of the cross-linkable structure during the in-situ micro-deformation and the irradiating of the cross-linkable structure.

2. The apparatus of claim 1, wherein the light irradiated to the cross-linkable structure has a wavelength spectrum of less than or equal to about 420 nm.

3. The apparatus of claim 1, further comprising:
   a force sensor and a displacement sensor connected to the probe.

4. The apparatus of claim 1, wherein the probe includes a tip positioned at one end of the probe, the tip being configured to contact the cross-linkable structure.

5. The apparatus of claim 1, wherein the probe is configured to repeatedly provide vibration to the cross-linkable structure during the in-situ micro-deformation.

6. The apparatus of claim 1, further comprising:
   a light-transmitting plate between the light source and the probe.

7. The apparatus of claim 1, wherein the light source and the probe are on an upper portion of the support plate.

8. The apparatus of claim 1, wherein
   the electronic controller is configured to adjust an intensity of the light source depending on the in-situ crosslink density.

9. An exposure equipment comprising the apparatus of claim 1.

10. A method for measuring an in-situ crosslink density, the method comprising:
    preparing a cross-linkable structure, the cross-linkable structure including a cross-linkable material and a crosslinking agent;
    irradiating the cross-linkable structure with a light configured to cross-link the cross-linkable structure;
    induce a stress-strain phase lag of the cross-linkable structure providing in-situ micro-deformation to the cross-linkable structure during the irradiating of the cross-linkable structure; and
    measuring the in-situ crosslink density of the cross-linkable structure from the stress-strain phase lag of the cross-linkable structure during the in-situ micro-deformation of the cross-linkable structure and the irradiating of the cross-linkable structure.

11. The method of claim 10, wherein the providing the in-situ micro-deformation to the cross-linkable structure is performed simultaneously with the irradiating of the light.

12. The method of claim 10, wherein the providing the in-situ micro-deformation to the cross-linkable structure comprises repeatedly vibrating the cross-linkable structure.

13. The method of claim 12, wherein the repeatedly vibrating the cross-linkable structure comprises vibrating a probe within an elastic section of the cross-linkable structure at a constant displacement in a direction perpendicular to an in-plane direction of the cross-linkable structure.

14. The method of claim 13, wherein the repeatedly vibrating the cross-linkable structure comprises vibrating the probe so that a strain of the cross-linkable structure is less than or equal to about 2%.

15. The method of claim 12, wherein the repeatedly vibrating the cross-linkable structure is performed at a frequency of about 0.05 Hz to about 100 Hz.

16. The method of claim 12, wherein a deformation depth of the cross-linkable structure due to the vibration is less than or equal to about 20% of a length of the cross-linkable structure.

17. The method of claim 10, wherein the measuring the in-situ crosslink density of the cross-linkable structure comprises calculating the in-situ crosslink density by Equation 1:

[Equation 1]

$$\text{Crosslink density}(\text{mol}/\text{cm}^3) = \frac{\Delta E' - \left\{\Delta E'' - (E''_{f_1} - E''_{f_2})\log\frac{f_2}{f_1}\right\}}{nRT'}$$

wherein, in Equation 1,
ΔE' is an amount of change in a storage modulus,
ΔE" is an amount of change in a loss modulus,
$f_1$ is a low frequency,
$f_2$ is a high frequency,
$E_{f1}"$ is an energy loss or a phase lag value at the low frequency,
$E_{f2}"$ is an energy loss or a phase lag value at the high frequency,
n is a proportional constant,
R is a gas constant, and
T' is a temperature (K).

18. The method of claim 10, wherein the light configured to crosslink the cross-linkable structure has a wavelength spectrum of less than or equal to about 420 nm with an intensity of greater than 0 W/cm² and less than or equal to about 10 W/cm².

19. The method of claim 10, further comprising controlling an intensity of the light based on the measured crosslink density.

20. The method of claim 10, wherein the cross-linkable material includes at least one of a siloxane moiety, a urethane moiety, an olefin moiety, an acrylic moiety, and a photosensitive resin.

21. A method of manufacturing a crosslinked product, the method comprising:
preparing a cross-linkable structure, the cross-linkable structure including a cross-linkable material and a crosslinking agent; and
cross-linking the cross-linkable structure by irradiating light onto the cross-linkable structure,
wherein the crosslinking of the cross-linkable structure comprises measuring an in-situ crosslink density of the cross-linkable structure by inducing a stress-strain phase lag of the cross-linkable structure by providing in-situ micro-deformation to the cross-linkable structure during the irradiating of the cross-linkable structure, and
wherein the measuring the in-situ crosslink density of the cross-linkable structure is determined from the stress-strain phase lag of the cross-linkable structure during the in-situ micro-deformation of the cross-linkable structure and the irradiating of the cross-linkable structure.

22. The method of claim 21, wherein the providing the in-situ micro-deformation to the cross-linkable structure is performed simultaneously with the irradiating of the light.

23. The method of claim 21, wherein the providing the in-situ micro-deformation to the cross-linkable structure comprises repeatedly providing vibration to the cross-linkable structure.

24. The method of claim 23, wherein the repeatedly providing the vibration to the cross-linkable structure comprises vibrating a probe within an elastic section of the cross-linkable structure at a constant displacement in a direction perpendicular to an in-plane direction of the cross-linkable structure.

25. The method of claim 23, wherein the repeatedly providing of the vibration to the cross-linkable structure comprises vibrating a probe so that a strain of the cross-linkable structure is less than or equal to about 2%.

26. The method of claim 23, wherein the repeatedly providing of the vibration to the cross-linkable structure is performed at a frequency of about 0.05 Hz to about 100 Hz.

27. The method of claim 23, wherein a deformation depth of the cross-linkable structure due to the vibration is less than or equal to about 20% of a length of the cross-linkable structure.

28. The method of claim 21, wherein the measuring the in-situ crosslink density of the cross-linkable structure comprises calculating the in-situ crosslink density of the cross-linkable structure by Equation 1

[Equation 1]

$$\text{Crosslink density}(\text{mol}/\text{cm}^3) = \frac{\Delta E' - \left\{\Delta E'' - (E''_{f_1} - E''_{f_2})\log\frac{f_2}{f_1}\right\}}{nRT'}$$

wherein, in Equation 1,
ΔE' is an amount of change in a storage modulus,
ΔE" is an amount of change in a loss modulus,
$f_1$ is a low frequency,
$f_2$ is a high frequency,
$E_{f1}"$ is an energy loss or a phase lag value at the low frequency,
$E_{f2}"$ is an energy loss or a phase lag value at the high frequency,
n is a proportional constant,
R is a gas constant, and
T' is a temperature (K).

29. The method of claim 21, wherein the light has a wavelength spectrum of less than or equal to about 420 nm with an intensity of greater than 0 W/cm² and less than or equal to about 10 W/cm².

30. The method of claim 21, further comprising controlling an intensity of the light based on the measured crosslink density.

31. The method of claim 21, wherein the cross-linkable material includes at least one of a siloxane moiety, a urethane moiety, an olefin moiety, an acrylic moiety, and a photosensitive resin.

32. The method of claim 21, wherein the crosslinking of the cross-linkable structure comprises:

disposing a mask on the cross-linkable structure, the mask having a plurality of light-transmitting portions and a light-blocking portion; and irradiating the light through the mask, wherein the light forms a plurality of crosslinked products, in the cross-linkable structure, at positions corresponding to the plurality of light-transmitting portions.

\* \* \* \* \*